United States Patent [19]

Krahenbuhl

[11] Patent Number: 5,016,623

[45] Date of Patent: May 21, 1991

[54] ANKLE SUPPORT

[76] Inventor: Doug W. Krahenbuhl, 878 E. Dupler Rd., Sandy, Utah 84070

[21] Appl. No.: 493,317

[22] Filed: Mar. 14, 1990

[51] Int. Cl.⁵ .................. A61F 3/00; A61F 13/06; A61F 5/37

[52] U.S. Cl. .................. 128/80 H; 128/166; 128/882

[58] Field of Search ............ 128/882, 166, 165, 166.5, 128/87 R, 87 C, 89 R, 87 A, 80 H

[56] References Cited

U.S. PATENT DOCUMENTS

| | | | |
|---|---|---|---|
| 1,129,525 | 2/1915 | Severy | 128/80 H |
| 4,280,488 | 6/1981 | Polsky | 128/80 H |
| 4,313,433 | 2/1982 | Cramer | 128/80 H |
| 4,547,981 | 10/1985 | Thais | 128/166 |
| 4,577,419 | 3/1986 | Chassaing | 128/166 |
| 4,621,648 | 11/1986 | Ivany | 128/166 |
| 4,651,726 | 3/1987 | Holland | 128/80 H |
| 4,729,370 | 3/1988 | Kallassy | 128/80 H |
| 4,753,229 | 6/1988 | Sutherland | 128/166 |
| 4,825,856 | 5/1989 | Nelson | 128/80 H |
| 4,878,504 | 11/1989 | Nelson | 128/166 |

Primary Examiner—Mickey Yu
Assistant Examiner—Michael Brown
Attorney, Agent, or Firm—M. Reid Russell

[57] ABSTRACT

An ankle support for use by persons recovering from an ankle injury or desiring to prevent ankle injury that includes a flexible heel foot support or shoe for fitting around the foot and ankle. A non-stretchable strap, that extends from beneath a fifth metatarsal area of the foot support or shoe and is fitted through a sleeve to pass over the outer ankle bone or lateral malleolus area of the foot support or shoe, and over an instep area and down to a ring mounted to the heel area support on the same side as the sleeve; and an arrangement to receive and maintain the strap in a taut condition to the ring.

6 Claims, 3 Drawing Sheets

ANKLE SUPPORT

BACKGROUND OF THE INVENTION

1. Field of the Invention

This invention relates to ankle support devices and is particularly concerned with a foot and ankle support that will effectively lock the ankle and foot so as to prevent damage or re-injury to the lateral ligaments of the ankle area.

2. Prior Art

It has long been recognized that the lateral ligaments are subject to injuries through twisting of the foot relative to the ankle. While such twisting can occur even during normal walking it is more apt to happen when an individual is involved in running sports or activities involving quick foot movement. Consequently, it is common that individuals involved in such activities use tape or elastic bandages to provide support between the foot and ankle to attempt to prevent such injuries. The taping and use of an elastic bandage wrap, if properly applied, is generally best left to a person having at least some training in their proper application. Furthermore, it is difficult for many persons, such as elderly, handicapped, and others to be able to apply tape and/or elastic bandages to their own ankles.

A number of ankle support devices have been proposed in the past that can be used in place of taping and/or elastic bandages and that will provide some measure of support for the ankle relative to the foot.

U.S. Pat. No. 3,970,083, discloses an ankle support that includes a jacket to fit around an ankle and includes elongated T-shaped stiffener strips at opposite sides thereof.

U.S. Pat. No. 4,367,733, discloses an ankle support that includes an elastic sock to fit on a foot and an elongate elastic panel that will wrap around the ankle and sock that is secured in place by Velcro fasteners.

U.S. Pat. No. 4,523,394, discloses an ankle support having a foot plate that extends from the heel forwardly of the arch, an ankle sleeve that surrounds the ankle of the user and includes flexible, lengthwise adjustable but not extensible bands interconnecting the foot plate and the ankle sleeve.

U.S. Pat. No. 4,556,054, also discloses an ankle support having a foot plate and an ankle sleeve. This disclosed device uses both resilient and non-resilient straps in conjunction with non-elastic means to secure the foot plate and ankle sleeve.

U.S. Pat. No. 4,597,395, discloses an ankle support that includes interconnected dorsal, plantar, and heel straps forming a heel lock that will conform to the heel shape of a user and a cross-over connected to the heel lock and that will cross in front of the ankle to be secured by fastener members.

U.S. Pat. No. 4,621,648, discloses an ankle support wherein straps are attached to a user's shoe. The shoe is affixed to the foot of a user and the straps are wrapped around the ankle and are secured by Velcro fasteners.

U.S. Pat. No. 4,753,229, discloses an ankle brace having a foot piece and an ankle cuff. Three straps are provided, each connected to the central lateral side of the foot piece. One strap extends from the heel end of the lateral side of the foot and across the front of the ankle and is secured to the ankle cuff at the anteriomedial aspect. The second strap extends from the outside arch side portion of the foot vertically upwards to a lateriral side portion of the ankle cuff. A third strap is attached from the front end of the outside of the foot around the rear of the ankle and attaches to the posteriormedial aspect of the ankle cuff.

While the aforementioned patents may have value in the prevention of ankle injuries to a user, I have found that more complete protection can yet be obtained utilizing the present invention that provides with a single strap arrangement greater support where and when needed than is provided by multiple strap configurations.

SUMMARY OF THE INVENTION

Objects of the Invention

Principal objects of the present invention are to provide an ankle support that is easy to install and that will provide effective support for the lateral ligaments of the ankle.

Features of the Invention

Principal features of the invention include the use of a foot support including an ankle enclosing flexible extension forming at least a partial soft shoe or conventional high top shoe and means to adjust the flexible extension snugly around the foot and ankle.

A non-stretchable strap has one end fixed to the foot support to be adjacent to the area of the foot support that receives the lateral or fourth or fifth metatarsal bones of a user and is passed through a sleeve that is fixed to the foot support. The sleeve is curved or angled to pass over the area of the foot support covering the outer ankle bone of the user and to direct the strap around the rear of the foot support, the strap to pass over the area of the support covering the inner ankle bone of the user. The strap then crosses over the instep area of the foot support with the free end thereof passed through a ring anchored to the outer heel of a user. The ring may be mounted to swivel to prevent strap bunching in the ring.

Other objects and features of the invention will become apparent from the following detailed description and drawings disclosing what is presently contemplated as being the best mode of the invention.

THE DRAWINGS

In the drawings:

FIG. 1 is a perspective view of the ankle support of the invention shown at one side and front and mounted on a user's ankle;

FIG. 2, a similar view, taken from the same side and at the rear;

FIG. 3, a fragmentary section view taken on the line 3—3 of FIG. 2;

FIG. 4, a perspective view taken from the other side and front and showing with arrows the user's foot twisted and the support countering that twisting action of the foot;

FIG. 5, a perspective view of another embodiment of ankle wrap of the invention taken from the front and one side; and FIG. 6, a perspective view of a high top shoe showing the ankle support configuration of FIGS. 1 and 2 incorporated therewith.

DETAILED DESCRIPTION OF THE INVENTION

Figure 1:
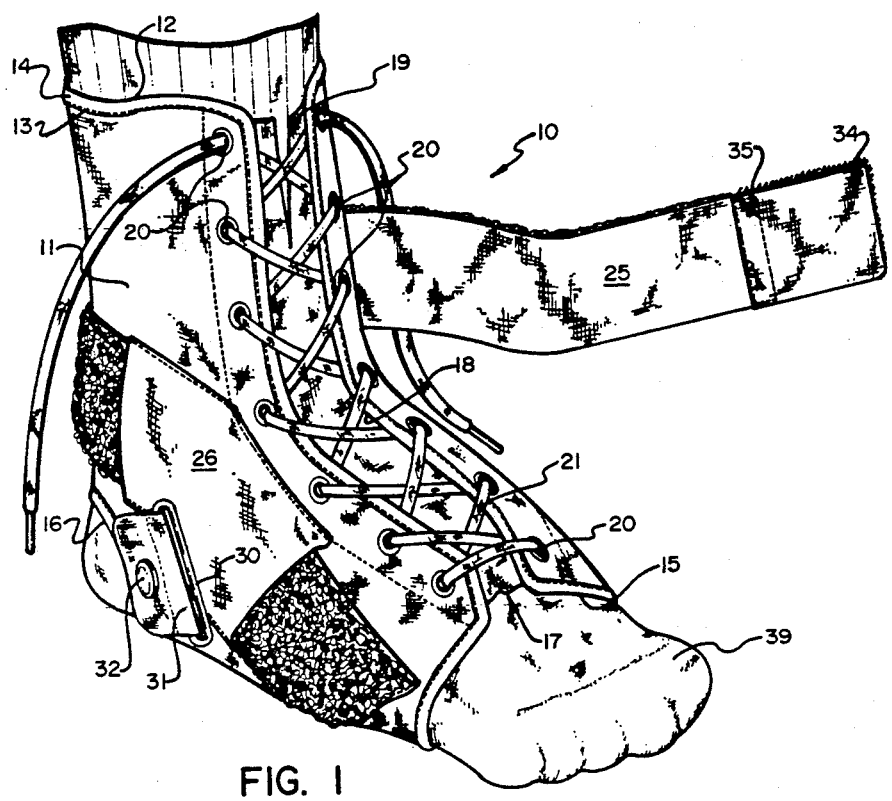
Figure 3:
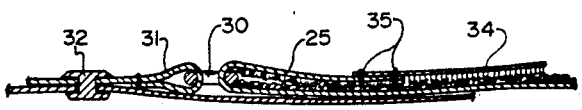
Figure 2:
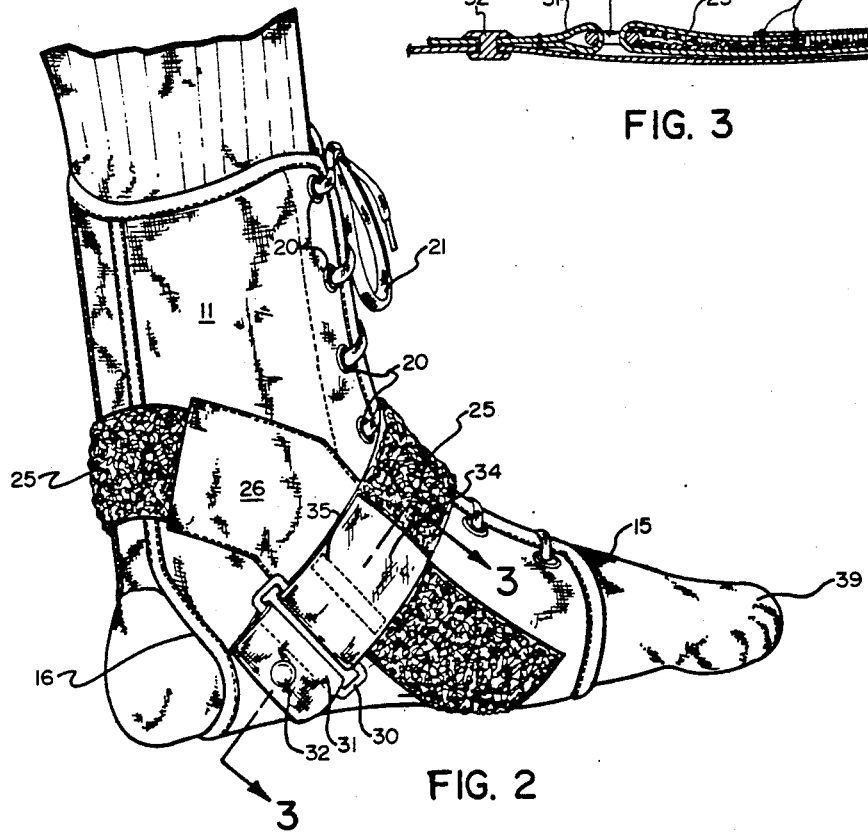

Referring now to the drawings:

In the illustrated preferred embodiment of the invention shown in FIGS. 1–4, the ankle support shown generally at 10 comprises a fabric shell foot support 11, hereinafter referred to as foot support, which may be made of seamed inner and outer layers of nylon 12 and 13 or other suitably strong material and with a padding material 14 such as cotton, arranged between the inner and outer layers. As shown, the foot support 11 is shaped as a high-topped shoe, that is open at the toe 15 and heel 16. The front 17 of the foot support is open at 18 with a tongue 19 that is attached to one side of the foot support to extend across the front opening 18 when the foot support is laced onto a user's foot. Spaced eyelets 20 are arranged along opposite sides of the front opening and a shoe lace 21 is provided for threading through the eyelets to secure the foot support to a user's foot in usual high-top shoe fashion.

A non-stretchable strap 25 is included that has one end attached to the outside surface of the foot support 11 in the area that fits over the fifth metatarsal bone of the user. The strap 25 is passed through a sleeve 26 that is secured to the outside of foot support 11 and is positioned to direct the strap 25 across the fifth metatarsal and is curved or angled upwardly and rearwardly over the area of the foot support that covers the outside ankle bone, or lateral malleolus, of a user. The sleeve 26 is curved or angled to direct strap 25 around the back of the foot support or heel cord, or achilles tendon such that the strap will pass over the area of the foot support that covers the inside ankle bone of a user. The strap is secured thereover when it is passed over or above the instep area of the foot support and the strap then passes through a ring 30. Which ring 30 may be but need not be pivotally fixed to the foot support outer surface, or lateral heel area.

The ring 30 is held in place by a flap 31 that is passed through the ring and has its ends anchored at the heel area of the foot support 11. Shown in FIG. 1 and 2 the ring is anchored by a rivet 32 though it could as well be secured thereto as by sewing, or the like. The flap 31 and ring 30 may be arranged to pivot about the rivet 32 to accommodate reception of the strap 25 end through ring 30 after the strap 25 has been passed across the instep. Adjustability is provided to prevent strap 25 from folding upon itself inside ring 30.

Strap 25 is removably attached to the ring 30 by passing a free end 34 of that strap through the ring and turning or bending the strap end back upon itself. A hook and loop fastener 35, such as that marketed under the trademark "VELCRO", is preferably used to secure the end of the strap to the strap surface, after that strap has been pulled tight.

The ankle support 10 is adapted for use on previously injured ankles or for protecting ankles against commonly occurring injuries.

Figure 4:
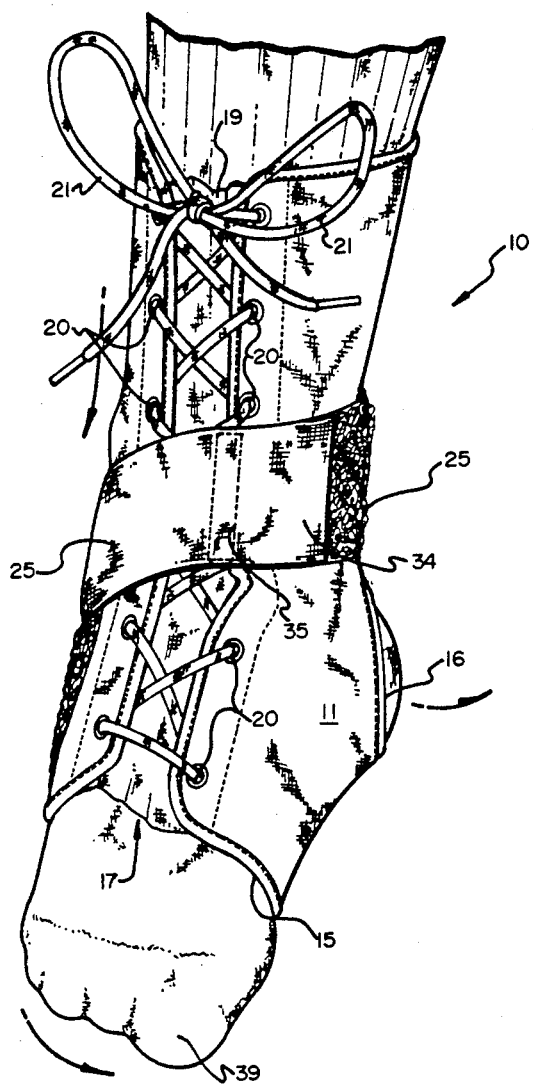

The foot 39 of a user wearing the ankle support 10, is shown with curved arrows, in FIG. 4 being turned in a manner that frequently will result in serious ankle injury. The foot 39 is shown rolling to the inside (inversion). Approximately 80% of all ankle sprains are sustained when the ankle is stressed in a position of inversion with the foot pointed down. This rolling of the foot and subsequent downward pulling and stretching of the lateral ankle ligaments is countered by the strap 25 that holds the ankle to the foot from the area of the fifth metatarsal bone and from the heel. As the foot rolls under, tension is applied to strap 25 at its origin at the fourth and fifth metatarsal area. If this force is followed along the strap around the ankle to its attachment to the heel buckle, one realizes that, due to the single support strap arrangement, a counterforce is produced at the heel, holding the heel up and out, or opposite to the direction of a force as would cause injury to the lateral ankle ligaments.

The ankle support 10 is readily worn inside a conventional shoe. As shown in FIGS. 1–4, it is constructed for use on the right foot of a user. It will be apparent that a support for use on the left foot would be constructed as a mirror image of that shown in FIGS. 1–4. Because the support is open in both the heel and toe areas the support can be used for feet of many sizes.

Figure 5:
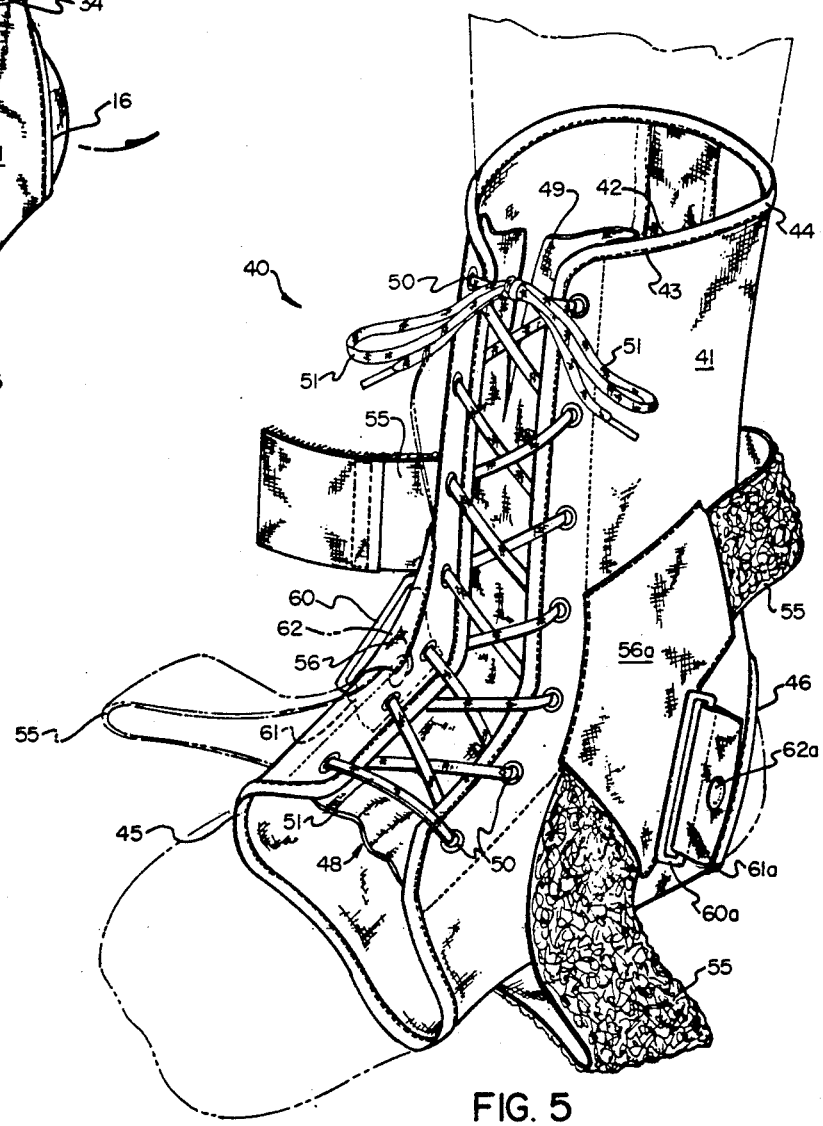

Another embodiment of the ankle support is shown in FIG. 5, as ankle support 40 that is constructed for use on either a right or left foot of a user. In this embodiment the fabric shell foot support 41 is constructed the same as the foot support 11 previously described. The foot support 41 is made of seamed inner and outer fabric layers 42 and 43 with a padding material 44 between them. The support is open at toe 45 and heel 46 and has a front opening 48 adapted to be covered by a tongue 49. Spaced eyelets 50 and a lace 51 for threading therethrough allow the support to be laced snugly onto a user's foot and ankle.

A non-stretchable strap 55, that corresponds to the strap 25 previously described, has one end sewn or otherwise affixed to the center bottom of the support 42. Two flexible sleeves 56 and 56a are respectively attached to opposite sides of the foot support 41, with each being curved upwardly and rearwardly on the support. The foot support 41 also has a pair of rings 60 and 60a affixed thereto. Thus, ring 60 is attached as by a flap 61 and a rivet 62 to one side of the support at the heel thereof and the ring 60a is attached by a flap 61a and a rivet 62a to the other side of the support at the heel area.

As in the previously described embodiment, strap 45 is adapted to be passed through one or the other of sleeves 60 or 60a and, as it is inserted through one of said sleeves, depending on whether the support is to be used on a right foot or a left foot of a user, the strap passes beneath and across the fifth metartsal bone of the user. The strap, after running through a sleeve 56 or 56a then passes over the instep area and is secured to a ring 60 or 60a on the same side of the support as the sleeve through which the strap is passed in the manner previously described.

The ankle support 40 is accordingly adapted for use on either foot of a user, for use in the same manner as the ankle brace 10.

Figure 6:
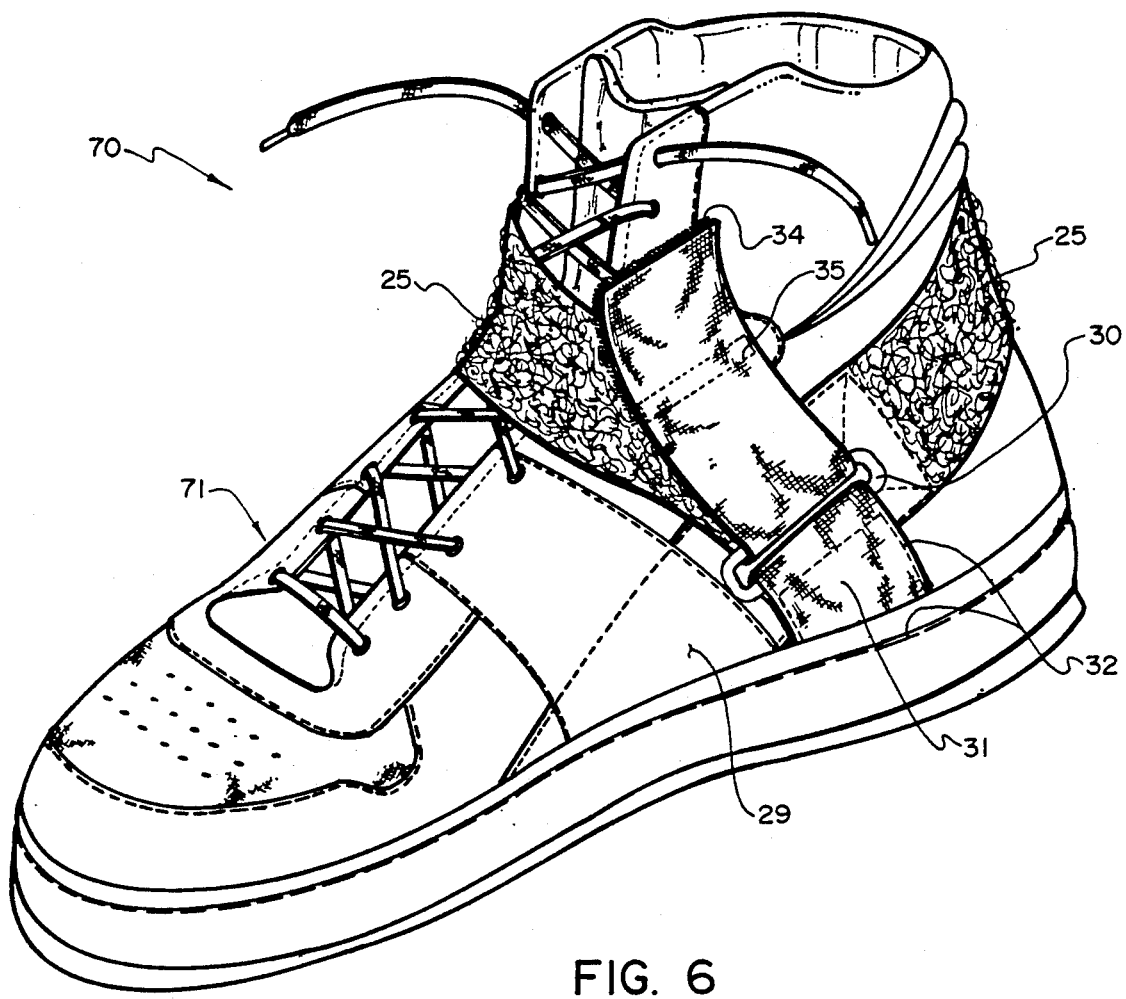

FIG. 6 shows still another embodiment of an ankle support 70. In this embodiment, a high top shoe 71 is the foot support, hereinafter referred to as shoe, that may be a canvas or leather high top, such as a basketball shoe, is substituted for the fabric shell foot support 11 of FIGS. 1 through 4. Accordingly, as shown in FIG. 6, the non-stretchable strap 25 is secured or attached at one end to the outside surface of shoe 71 in the area that fits over the fifth metatarsal bone of the user. The strap 25 is passed through sleeve 26 that is outside of the shoe 71 to direct the strap 25 across the fifth metatarsal, functioning as described hereinabove with respect to FIGS. 1 and 4. The strap 25, directed by sleeve 26, passes around the back of the wearer's foot, or achilles tendon, and over the inside ankle bone and across the top of the foot and through ring 30 which ring is shown attached by a flap that is secured to the shoe and is fitted through the ring, and folded back upon itself. The overlapping lap sections are sewn at 32 to fix the ring 30 to the shoe's outer surface, or lateral heel area. Which ring in this embodiment may also be pivotally fixed to the shoe, rather than sewn within the scope of this disclosure. The strap 25 is fitted through ring 30 and is folded back in itself. A VELCRO type hook section 34 is provided on the strap for coupling to an opposite VELCRO type mat surface 35 to maintain the strap end to the strap body, functioning as described above with respect to a discussion of FIGS. 1 through 4.

Although a preferred form of my invention has been herein disclosed, it is to be understood that the present disclosure is by way of example only and that variations are possible without departing from the subject matter coming within the scope of the following claims and a reasonable equivalency thereof, which subject matter I regard as my invention.

I claim:

1. An ankle support comprising a foot support that is open at a top and has an open front; means to fit said foot support snugly to a user's foot, including means to close said foot support open front; a non-stretchable support strap secured to said foot support to extend across an area of said foot support that is over a user's fifth metatarsal bone; a flexible sleeve secured at its edges onto said foot support surface over the outer ankle bone and is bent to form a straight sleeve that is angled upwardly rearwardly of said support to direct said strap fitted therethrough across the outer ankle bone area and around the achilles tendon and across the inside ankle bone; and means affixed to said foot support adjacent to the heel area and the same side as said flexible sleeve to receive and to secure said strap.

2. An ankle support as in claim 1, wherein the foot support is a fabric shell that is open at the heel.

3. An ankle support as in claim 1, wherein the foot support is a high top shoe.

4. An ankle support as in claim 1, wherein the means affixed to the foot support adjacent to the lateral heel area comprises a ring; a flap through said ring; and means for attaching said flap to said foot support.

5. An ankle support as in claim 4, wherein the strap is affixed to the foot support in the fifth metatarsal area.

6. An ankle support as in claim 1, wherein, for an ankle support for use on either right or left foot, a sleeve is provided at each side of the foot support; and the strap is affixed to the bottom center of said foot support and will cross the foot fifth metatarsal area when inserted into one of said sleeves.

* * * * *